US009295827B2

(12) United States Patent
Thorne

(10) Patent No.: US 9,295,827 B2
(45) Date of Patent: Mar. 29, 2016

(54) TWISTED SLIT VALVE

(71) Applicant: Gale Harrison Thorne, Bountiful, UT (US)

(72) Inventor: Gale Harrison Thorne, Bountiful, UT (US)

(*) Notice: Subject to any disclaimer, the term of this patent is extended or adjusted under 35 U.S.C. 154(b) by 395 days.

(21) Appl. No.: 13/872,828

(22) Filed: Apr. 29, 2013

(65) Prior Publication Data
US 2014/0319393 A1 Oct. 30, 2014

(51) Int. Cl.
*A61M 39/26* (2006.01)
*A61M 39/24* (2006.01)
*A61M 39/10* (2006.01)

(52) U.S. Cl.
CPC ............... *A61M 39/26* (2013.01); *A61M 39/24* (2013.01); *A61M 2039/1033* (2013.01); *A61M 2039/1077* (2013.01); *A61M 2039/2433* (2013.01)

(58) Field of Classification Search
CPC ............... A61M 39/24; A61M 39/26; A61M 2039/1077; A61M 2039/1033; A61M 2039/2433; A61M 2039/0633; F16K 15/147
USPC ............ 251/147, 149.1–149.7; 604/247–249, 604/256, 533, 537; 137/512.15, 493.1, 137/844–850, 614.03–614.04
See application file for complete search history.

(56) References Cited

U.S. PATENT DOCUMENTS

| 4,673,393 | A | * | 6/1987 | Suzuki | A61M 39/0606 138/89 |
| 4,895,565 | A | * | 1/1990 | Hillstead | A61M 39/0606 137/849 |
| 5,167,637 | A | * | 12/1992 | Okada | A61M 39/0606 251/149.1 |
| 5,176,652 | A | * | 1/1993 | Littrell | A61M 39/0606 137/849 |
| 5,350,363 | A | * | 9/1994 | Goode | A61M 39/0606 604/167.04 |
| 5,807,348 | A | * | 9/1998 | Zinger | A61M 39/045 604/246 |
| 7,766,304 | B2 | | 8/2010 | Phillips | |
| 8,803,805 | B2 | | 9/2010 | Faugrow | |
| 7,938,805 | B2 | | 5/2011 | Harding et al. | |
| 8,753,317 | B2 | * | 6/2014 | Osborne | A61M 39/0606 604/164.01 |
| 2004/0015185 | A1 | * | 1/2004 | Ewers | A61B 17/0293 606/213 |
| 2004/0035816 | A1 | * | 2/2004 | Okiyama | A61J 1/1406 215/247 |
| 2008/0172003 | A1 | * | 7/2008 | Plishka | A61M 39/045 604/246 |
| 2013/0310808 | A1 | * | 11/2013 | Stout | A61M 39/10 604/537 |

* cited by examiner

*Primary Examiner* — Marina Tietjen
(74) *Attorney, Agent, or Firm* — Gale H. Thorne

(57) ABSTRACT

A self-closing twisted slit valve which is opened by compression inside a receiving tapered female orifice. For luer fittings, internal taper of a female luer fitting provides sufficient distortion of an asymmetrical valve to distort a closed, preferably planar slit to a patent fluid pathway. The slit may be opened by valve displacement into a female connector orifice or by being pierced by a blunt cannula. The valve may be effectively used for both needleless connectors and for needleless connector adapters.

9 Claims, 6 Drawing Sheets

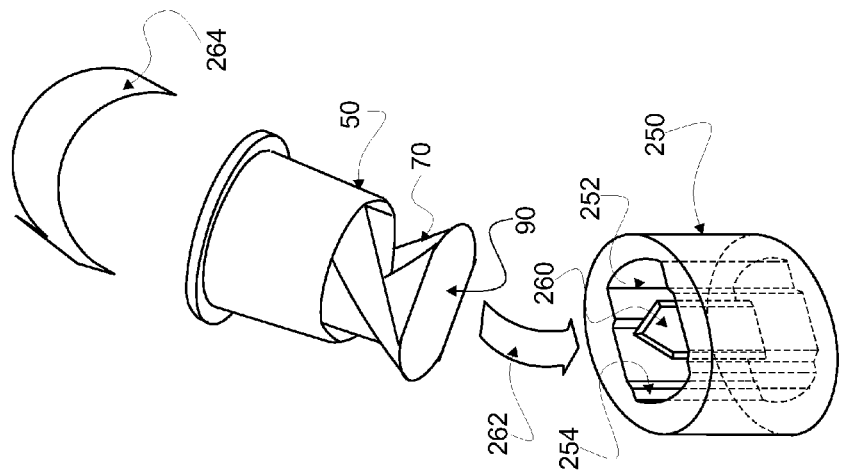
Figure 14
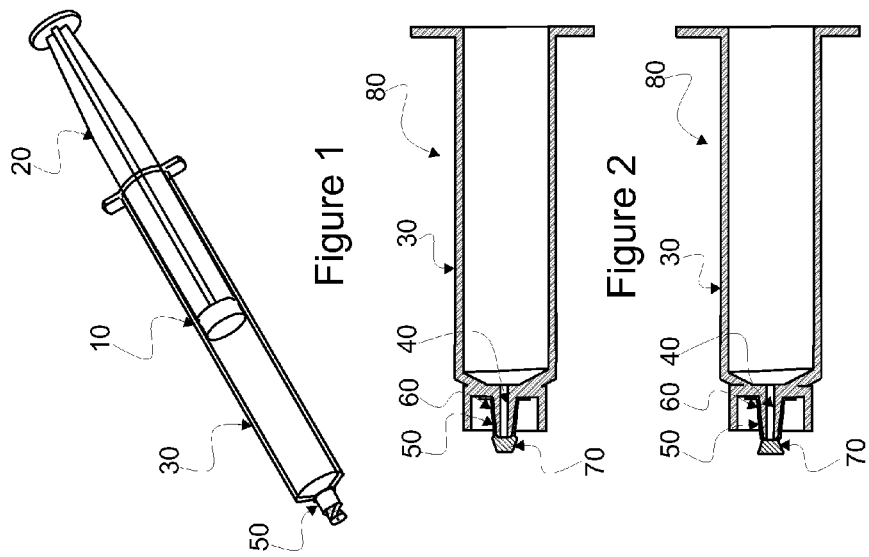
Figure 1
Figure 2
Figure 3

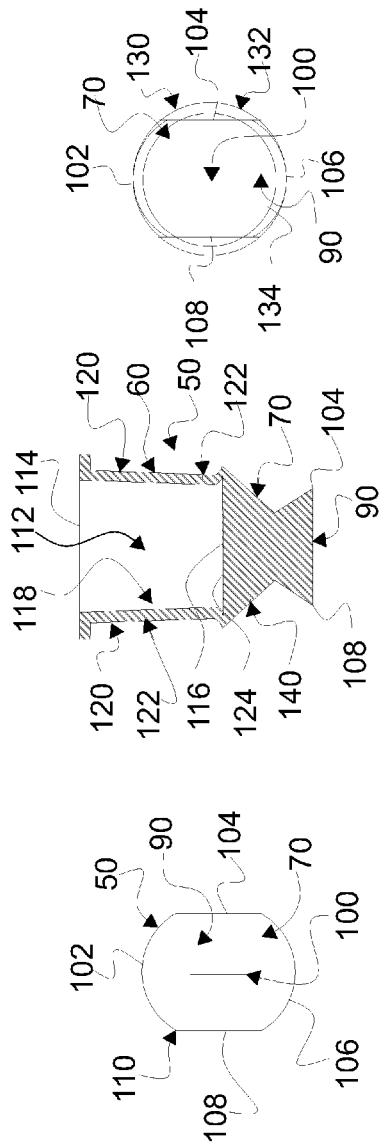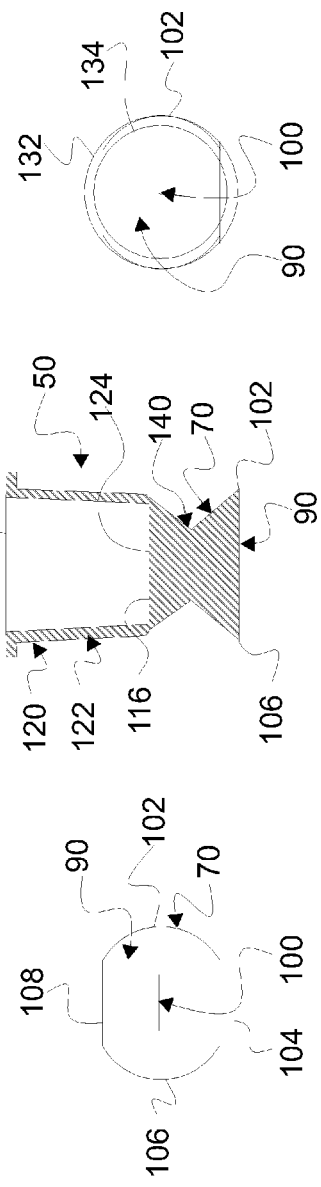

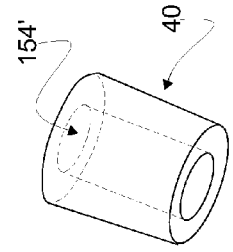
Figure 8
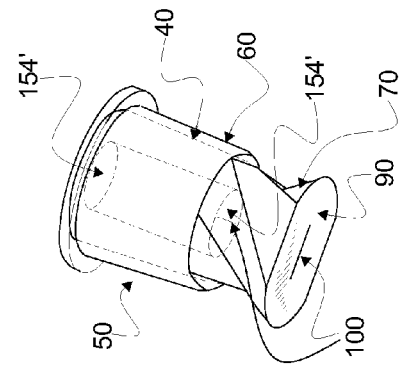
Figure 12
PRIOR ART
Figure 7
Figure 11
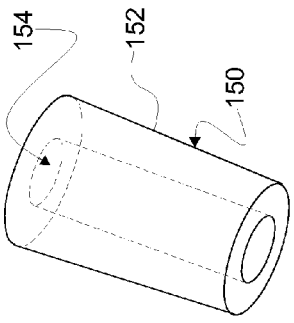
Figure 6
Figure 10
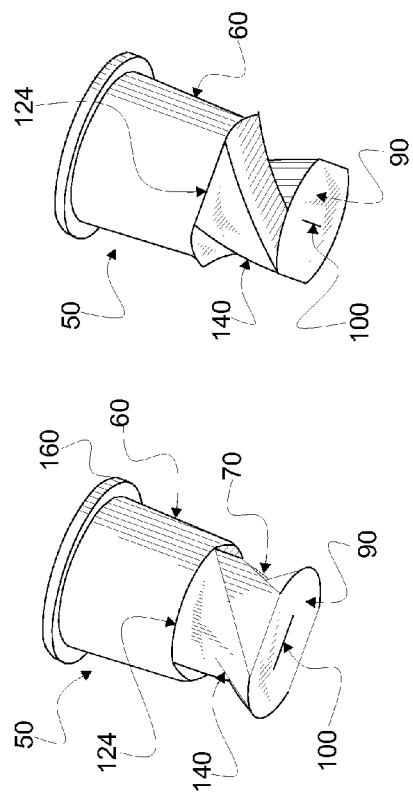

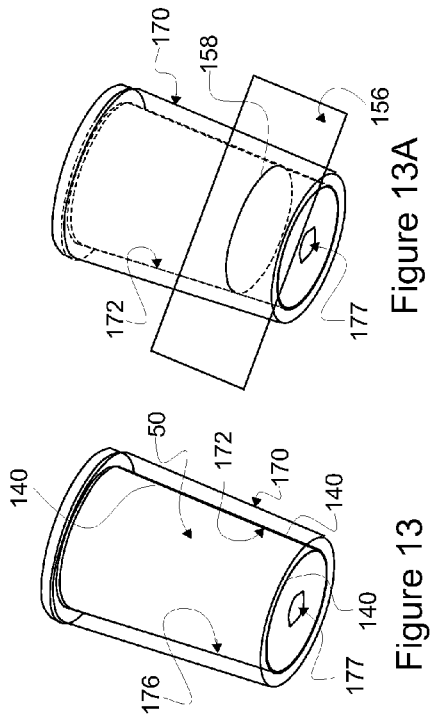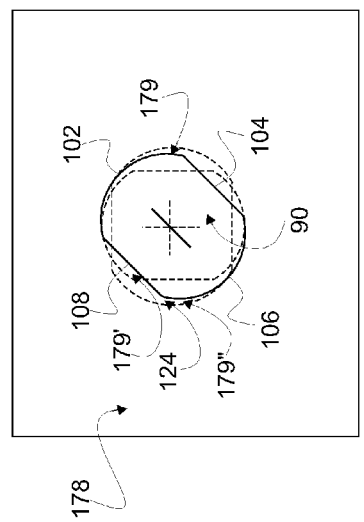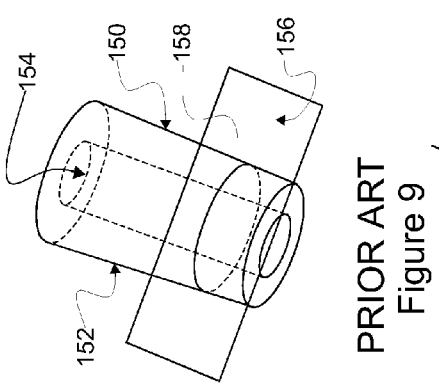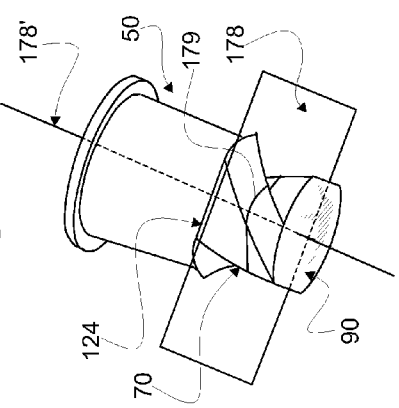

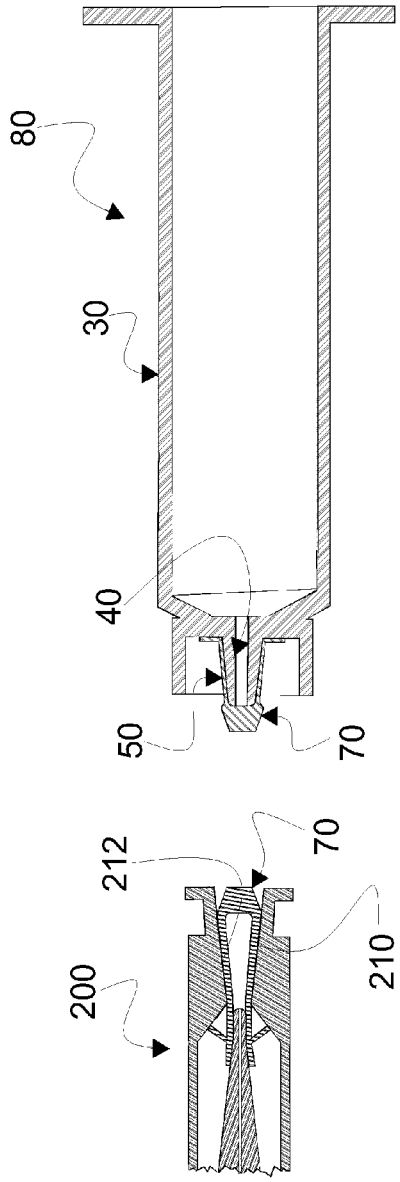
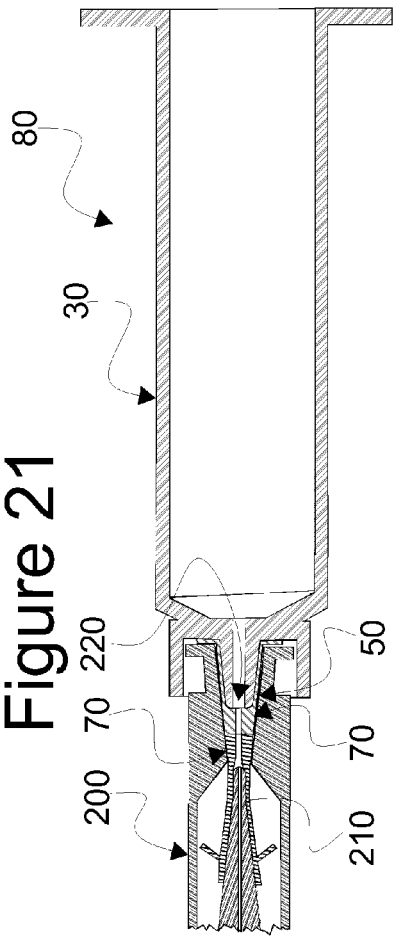
Figure 21
Figure 22

TWISTED SLIT VALVE

FIELD OF INVENTION

This application relates to self-closing valves in general and to male and female valves, for medical luer fittings, which are opened by insertion of a portion of the male valve into a predetermined depth within a female luer fitting, in particular. The invention also relates to slit valves, and, in particular to slit valves which comprise slits which may not be planar and which are opened by medially directed compressive forces about the exterior of the valve and, once compression is removed, self close to stop fluid flow.

BACKGROUND AND DESCRIPTION OF RELATED ART

While the present invention broadly applies to self-closing valves, it has particular application to self-sealing male and female luer valves used in medical applications.

Two primary prior art patents well disclose the need and opportunity for a male luer valve which is opened upon insertion into a female luer fitting. The first, U.S. Pat. No. 7,766,304 B2 issued to John C. Phillips (Phillips 304) Aug. 3, 2010 and titled, SELF-SEALING MALE LUER CONNECTOR WITH BIASED VALVE PLUG discloses a male luer connector for connection with a female luer connector. Phillips 304 further discloses a device comprising a tubular male body and a surrounding displaceable cuff. A valve plug is slidably disposed within the housing and formed to, in a first state, seal a communicating hole and, in a second state, be displaced to open the hole for fluid communication. Closure is biased to occur by an elastomeric coupling which communicates with the plug.

The second, U.S. Pat. No. 7,803,140 B2 issued to Thomas F. Fangrow, et al (Fangrow 140) Aug. 16, 2011 and titled, MEDICAL CONNECTOR discloses two primary designs for a male luer connector for connection with a female luer connector. The first design comprises a plugging component which is offset to open a valve for fluid flow. The second design discloses a slit valve which is opened for flow by insertion of a piercing part.

Such male valves provide barriers for infecting bacteria and debris, but perhaps more importantly provide a self-closing barrier and, thus, a closed system against inadvertent leakage, wherein product associated with such leakage might be a hazardous drug. It is important to note that such male valves should only be disposed in an open state while the valve is inserted into a complementary female fitting. At this date, all contemporary commercial male adapters for needleless connectors employ a linear displacement mechanism which removes a "plug" from a hole when the valve is inserted into a female luer fitting. Such mechanisms are commonly complex in structure and, therefore, result in an elevated component cost. Generally within the scope and meaning of this Application, the term male luer adapter shall be used as a reference for such male valves.

Further, male luer adapters such as those provided as examples, supra, are actuated to an open state by either a displacement of a plug within a hole or by a slit of a valve being parted by insertion of a piercing part. In the case of plug displacement, such is known to often result in a small droplet of liquid remaining resident at the exterior of the hole and plug site upon closure.

Slit valves are widely used and well understood in valve art to be most often made by slitting thin membrane material. Such valves are commonly used in medical practice, for example, in stop valves which are permissive to flow in only one direction. Such valves generally have no moving parts, except for membrane displacement to permit unidirectional flow.

Other examples of uses of slit valves in medical art is the application of slit valves in needleless medical connectors. Such connectors may be opened by linear displacement against a hollow probe which displaces lips of a slit to permit fluid flow, or may be released to open when displaced from a luer fitting.

Within the scope of this application, terms which are absolute, such as round, unreactive, closed, are understood to be permissive of manufacturing and physical limitations which, while functionally permitting a desired function, do not absolutely comply with definition of the term.

BRIEF SUMMARY AND OBJECTS OF THE INVENTION

In brief summary, this novel invention alleviates known problems related to opening and closing male luer adapters when requiring a portion of the valve be displaced longitudinally relative to a part into which the valve is being inserted. Central to the instant invention is a valve body having asymmetrical side dimensions formed about a twisted or spiral slit, the valve body being formed to conform with the nature of the slit such that, preferably, a predetermined orthogonal distance from slit to outer surface of the valve body is substantially constant. The valve body is formed of a flexible, incompressible material having memory which maintains an unconstrained body in its originally formed (e.g. molded) state. Of course, for medical applications, the material must also be unreactive to physiological fluids. Such a material is butyl rubber which is used in contemporary syringe plunger applications.

The valve body may be prepared for slitting by rotating the body to a planar or untwisted state while displacing it into an open cavity. The cavity is sized and shaped to straighten and untwist the body as it is displaced therein. As such, the material from which the body is formed must be sufficiently flexible to permit the body to be conformably inserted into the slitting cavity and, thereby, straightened within the cavity.

While the valve body is so inserted and straightened, a substantially straight or planar slit can be incised into the body. To accomplish such, a slitting knife or laser ray, for examples, may be displaced through a predetermined portion of the body to form the slit. Upon removal of the body from the cavity, memory of material from which the body was formed reorients and twists the body again to its original shape, forming a twisted slit. Being so twisted, the closed slit resists, sufficiently, effects of pressure internal to the body, to form a normally closed valve.

Opening of the valve can be accomplished in either of two modes. The first mode is by compressive distortion of the body to deform the slit from a generally planar state to a more compact curved state, thereby creating an open fluid pathway. As the slit, though twisted is disposed completely through the valve, a hollow tubular cannula can be displaced through the twisted planar pathway to provide a path for fluid flow, thereby changing the valve to an open state. Note, that, in either case restructuring the body from a compressed state or removing the hollow tubular object results in automatic valve closure.

In the case of valve opening by body distortion, the exterior surface circumference of each body crosscut segment about the slit can be formed to have a predetermined dimension. Likewise, the dimensions of each body crosscut segment will have a predetermined length and width, dependent upon slit length upon which a crosscut circumference conforms. The valve body is preferably designed such that the crosscut circumference is equal along its length to the associated interior surface of a hollow tapered tube (e.g. a female luer fitting) in which the valve is displaced for opening.

In general, a valve device body, according to the instant invention, has two ends. The first end comprises the twisted slit valve which is formed to be used as a fitting element of a releasable connector. The second end comprises a means for forming a communicating, connecting part whereby fluid may be displaced through the valve. If, for example, the slit valve is part of a stand alone male luer adapter, such as those used in common medical applications, the first end would serve as a male luer fitting while the second end may be formed as a female luer fitting having a portion which is attachable to a fluid source implement. In such a case, as the male luer fitting portion of the device is inserted into an associated female luer fitting, flexibility of the slit valve allows material to be distorted to conform to the inner circumference of the female luer fitting, resulting in formation of a through hole along the path of the slit and thereby opening the valve. It should be obvious to those skilled in incompressible materials art that the circumference of each cross section of the valve should be of the same dimension as the circumference of the cross section of the associated interior of the luer fitting when the valve is fully inserted into the female fitting to assure a good, sealing fit.

In the case of valve opening by displacement of a hollow tube or cannula through the slit pathway, it should be noted that no compressive body distortion by an exterior force is required, although such distortion may be advantageously applied to provide easier access to the slit pathway. Also it should be noted that such displacement may be in either direction through the slit pathway. Even though the slit is closed and twisted and the valve is undeformed by exterior force, a blunt cannula corresponding in circumference of outer surface to an effective diameter of a slit of predetermined length may be displaced through the valve when closed. The pathway formed by such cannula displacement effectively opens the valve while the cannula resides therein. Removal of the cannula permits the valve to self-reclose.

Accordingly, it is a primary object to provide a valve which is made from a material which is incompressible, elastic and deformable to be compressibly opened when displaced into an elongated tube having an inside diameter which conformably deforms the valve to open along an imbedded slit.

It is a very important object to provide a normally closed valve comprising but a single molded part which can be affixed to a male luer fitting and opened by displacement into a female luer fitting.

It is an equally important object to provide a normally closed valve comprising but a single part which resides within a female tapered luer fitting and which is opened by deeper displacement into the female luer fitting.

It is an important object to provide a normally closed and self-sealing slit valve which has two distinct and independent opening modes (i.e. by displacement into a hollow tapered tube of predetermined internal surface circumference and by displacement of a blunt cannula through the valve).

It is an object to provide valve which is displaced to an open state by application of a medially directed force causing compressive deformation.

It is another object to provide a self-sealing valve having a body which is molded from an incompressible, flexible and elastic material.

It is an object to provide a method for making a twisted slit within a molded twisted valve body.

These and other objects and features of the present invention will be apparent from the detailed description taken with reference to accompanying drawings.

BRIEF DESCRIPTION OF THE DRAWINGS

FIG. 1 is a conventional medical syringe with a twisted luer valve affixed to a fluid communicating end of the syringe.

FIG. 2 is a cross section of another conventional medical syringe with a luer lock fitting affixed at the fluid communicating end and a twisted luer valve affixed to the associated male luer of the syringe.

FIG. 3 is a cross section of the syringe seen in FIG. 2, but rotated 90° to show variation in shape of the attached valve.

FIG. 4 is an elevation of an exposed surface of a twisted slit valve, oriented in a first rotational orientation.

FIG. 4A is a cross section of a twisted slit valve device which may be affixed to a male luer fitting to provide a closed valve which is opened, for example, by insertion into a female luer fitting.

FIG. 4B is an elevation of the exposed surface of the twisted slit valve seen in FIG. 4 plus outer and inner diameters of a female luer fitting into which the twisted slit valve is displaced for opening and subsequent fluid communication.

FIG. 5 is an elevation of the exposed surface seen in FIG. 4, but rotated 90°.

FIG. 5A is a cross section of the twisted slit valve device seen in FIG. 4A, but rotated 90° to show relative variances in linear dimensions due to rotation.

FIG. 5B is an elevation of the surface of the twisted slit valve and inner and outer diameters of the luer fitting similar to FIG. 4B, but rotated 90°.

FIG. 6 is a perspective of a twisted slit valve.

FIG. 7 is a perspective of a PRIOR ART male section of a conventional luer fitting.

FIG. 8 is a perspective of a male section of a luer fitting reduced in diameter and length, relative to the fitting seen in FIG. 7, for being affixed to a twisted slit valve device.

FIG. 9 is a perspective of the PRIOR ART male section seen in FIG. 7 with a plane, orthogonally disposed relative the long axis of the section, to cut across and thereby demonstrate the circumference of an associated exterior surface along a perpendicular line of intersection.

FIG. 10 is a perspective of a twisted slit valve device similar to the twisted valve device seen in FIG. 4A.

FIG. 10A is a perspective of the twisted slit valve device seen in FIG. 10 with a plane, orthogonal to the long axis of the device, disposed to cut through a mid-portion of the associated valve.

FIG. 10B is an elevation of the plane shown in FIG. 10A with the crosscut of the plane and valve seen in solid lines and with two other crosscuts from other valve sites disposed along the long axis of the device seen in dashed lines.

FIG. 11 is a perspective of a twisted slit valve device similar to the twisted valve device seen in FIG. 10, but rotated 90°.

FIG. 12 is a perspective of the twisted slit valve device of FIG. 10 shown as transparent to permit the male section seen in FIG. 8 to be seen disposed therein.

FIG. 13 is a perspective of a twisted valve device, such as the valve device seen in FIGS. 10 and 11, disposed within a section of a female luer fitting and compressed by force of insertion to conform to the internal surface of the female luer fitting and to form an associated slit into an open fluid pathway.

FIG. 13A is a perspective of the combination seen in FIG. 13 with a plane, similar to the plane of FIG. 9 orthogonally disposed relative the long axis of the section, to demonstrate the circumference of associated exterior surface of the section along the line of intersection with the plane.

FIG. 14 is a perspective of a freshly molded, twisted slit valve device, similar to the device seen in FIG. 7, disposed for rotational displacement into a blade containing cavity to cause the twisted valve to be rotated to a planar state while incising a planar slit through the valve body.

FIG. 21 is a cross section of a medical syringe with a twisted slit valve affixed thereto, as seen in FIG. 2, and a portion of a needleless connector which also comprises a twisted slit valve device.

FIG. 22 is a cross section of the syringe and needleless connector joined by male fitting into female fitting insertion to open both twisted slit valves.

DETAILED DESCRIPTION OF THE ILLUSTRATED EMBODIMENTS

Figure 15:
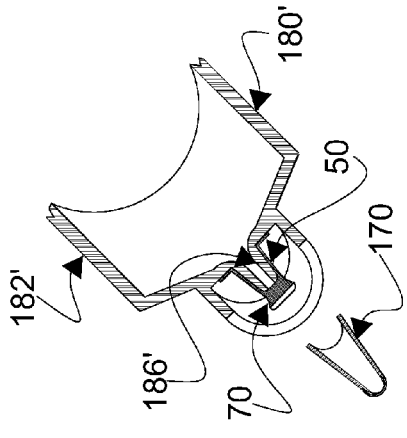
FIG. 15 is a cross section of a portion of a PRIOR ART conventional luer lock syringe.

While the instant invention disclosed herein is applicable to a wide variety of male/female insertion type fluid connectors, the detailed description provided herein is focused upon luer fittings for purposes of brevity and clarity. In this description, the term proximal is used to indicate the segment of the device normally closest to the object of reference. The term distal refers to the opposite direction. Reference is now made to the embodiments illustrated in FIGS. 1-22 wherein like numerals are generally used to designate like parts throughout.

As seen in FIG. 1, a conventional medical syringe (generally numbered 10) comprises a plunger/stem assembly 20 and a barrel (generally numbered 30). Barrel 30 further comprises a male luer fitting 40 (not seen in FIG. 1, but seen in cross section in FIGS. 2 and 3).

Referencing FIG. 1 once more, a twisted slit valve device 50 is disposed about fitting 40 to cap and close fluid flow into or out of barrel 30. While dimensions of syringe barrel 30 in FIGS. 2 and 3 are seen to be different than barrel 30 seen in FIG. 1, dimensions of male luer fitting 40 are, by specification the same.

It is preferred for device 50 to be disposed and securely affixed to luer fitting 40 (such as by adhesion). Device 50 comprises a sleeve portion 60 and a valve portion 70. The same syringe barrel 30 and device 50 (forming combination 80) are seen in both FIGS. 2 and 3. The combination 80 in FIG. 3 is rotated 90° relative to combination 80 seen in FIG. 2 to demonstrate asymmetric structure of valve portion 70.

Reference is now made to FIG. 4 wherein an exposed face 90 of valve portion 70 is seen. Hereafter valve portion 70 may be referenced more simply as valve 70. A slit 100 is seen exiting at face 90. Circumferentially disposed about slit 100 are segments of sides 102, 104, 106 and 108 of external surface 110. Segments of sides 102 and 106 are preferably of equal length. Segments of sides 104 and 108 are also preferably of equal length. The combined length of segments of sides 102, 104, 106 and 108 are designed to be a predetermined length as disclosed in detail hereafter. Slit 100 is preferably disposed equidistant from each segment of sides 104 and 108 and from a mid point of each arc of segments of sides 102 and 106. Length of slit is also predetermined as disclosed hereafter.

As seen in FIG. 4A, sleeve 60 of device 50 comprises a cup 112 which open at one end 114 and closed by valve 70 at the other end 116. Further sleeve 60 comprises an internal surface 118 which is sized and shaped to snugly engage a female luer fitting 40 (seen in FIGS. 2 and 3) disposed therein. Side structure 120 disposed between internal surface 118 and external surface 122 of cup 112 is of uniform thickness to maintain a shape which snugly engages an associated female luer fitting. The double frustoconical convergent/divergent shape of valve 70 represents a 90° twist in construction. While it is not necessary to employ a 90° twist, any twist increases force necessary to force slit 100 apart and thereby decreases inadvertent patency of valve 70. It should be noted that slit 100 is not seen in the cross section of FIG. 4A as slit 100 follows a twisted path from external face 90 to an internal face 124 which corresponds with end 116.

In FIG. 4B, face 90 is seen preparatory to being displaced into a female luer fitting 130. Internal surface dimensions are seen as circle 132 for an external female orifice opening of luer fitting 130 and smaller circle 134 for a more distal orifice portion. Relative dimensions of circles 132 and 134 demonstrate variation in orifice diameter of a female luer fitting due to luer taper.

Note that lateral extension of segments of sides 102 and 106 substantively correspond to the diametric size of circle 132. While a valve 70 may be made of material supple enough to be displaced into a female luer fitting with a relatively smaller opening orifice diameter 132, care should be taken to assure no inappropriate distortion of face 90 occurs at insertion. Note also that as valve 70 is displaced into fitting 130, decreasing diameter of fitting 130 compresses segments of sides 102 and 106. This compression forces segments of sides 104 and 108 outward to open slit 100 along the entirety of the inserted part. Of course, the dimensions of the external surface 140 (see FIGS. 4A and 5A) should be shaped to conform with the pitch of female fitting 130, as further disclosed hereafter.

FIGS. 5, 5A and 5B are provided for visualization of relative dimension variances upon a 90° rotation of device 50 relative to FIGS. 4, 4A and 4B. Note position and variances in dimension of faces 90 and 124 between FIGS. 4A and 5A.

A general form of a twisted slit valve (numbered 70') is seen in FIG. 6. A plurality of lines (generally numbered 140') are drawn from points of similar origin from opposing faces 90' and 124' to represent form of twist. As stated supra, while this valve discloses a 90 degree twist, any angle of twist which assures closure against forces of pressure which could open the valve may be used within the scope of the instant invention.

Male luer fittings currently in general use in the medical community are well specified to assure compatibility across a wide spectrum of manufacturers and uses. As seen in FIG. 7, a male section of a PRIOR ART luer fitting 150 comprises a tapered outer surface 152 and a through hole 154 through which fluid is dispensed. Surface 152 is sized and shaped to sealingly engage a female luer fitting. As such, the taper is defined to be 6°, taking taper of opposing sides into account. Thus the change in diameter from entry orifice (as by example in FIG. 4B) 130 along tapered outer surface 152 is defined as follows:

$$d = d_{max}(1 - 2 \cdot x \cdot \tan(\alpha))$$

Where:
$d_{max}$=the diameter at the exposed female luer fitting orifice at a site of maximum circumference
x=a distance displaced within the female luer fitting along a long axis of hole 154 away from the exposed luer fitting orifice
α=angle of side taper (for a luer fitting α=3°

Thus, as seen in FIG. 9, if a plane 156, orthogonally disposed relative to long direction of hole 154 is passed through fitting 150, a circle 158 is defined by the intersection between plane 156 and surface 152. For a male luer fitting to fit acceptably within a female luer fitting, the exterior surface diameter at every such plane 156, along distance x, must be so sized. For this reason, it is critically important that the surface dimension of a valve disposed to be a sealing insert within a female luer fitting have the same surface diameter dimensions.

A section of a male luer fitting 40 (see FIGS. 2, 3 and 8) is generally shorter than male luer fitting 150 (see FIG. 7) of a conventional syringe. Luer fitting 40 is shortened to permit additional length to be added by valve 70 of device 50. Also, diameter of fitting 40 is reduced to permit side structure 120 (see FIG. 4A) to be affixed to fitting 40 while retaining appropriate diameter and surface dimensions for an acceptable connection inside a female luer fitting.

As may be better seen in FIG. 10, in addition to sleeve 60 and valve 70, device 50 may comprise a ring 160 which may be used as a rim against which force may be applied to affix sleeve 60 of device 50 about a male fitting 40. Reference is made to FIG. 12 wherein device 50 is seen as transparent to provide a view of a sleeve 60 disposed about a male luer fitting 40. Note that hole 154' (seen in FIGS. 8 and 12) is in line with slit 100. For visualization of valve 70 structure, device 50 is seen to be rotated 90° in FIG. 11 relative to device 50 in FIG. 10.

In general, each female luer fitting 170 comprises an open, tapered tube 176 from circular orifice 172, as seen in FIG. 13. When device 50 is fully inserted into a female luer fitting 170, as seen in FIG. 13, compressive forces applied by wall taper within fitting 170, shapes exterior surface 140 to conform with dimensions of orifice 172 and associated tube 176. Such provides the same sealing interface which occurs within a conventional luer fitting connection when material used for valve 70 is pliant and incompressible. For this reason, the dimensions of the side surface of valve 70 must be essentially the same as dimensions of inner surface of orifice 172 to assure integrity of such a connection. Compressive pressure about twisted slit valve 70 parts slit 100 to provide an open pathway 177 (i.e. a through hole).

Referencing FIG. 10A, a plane 178 is seen to be orthogonally disposed relative to a medially disposed long axis 178' through valve 70 of device 50 midway between faces 90 and 124 (For reference, see FIGS. 4A and 5A.). An outline of a crosscut 179 is defined by the intersection between valve 70 and plane 178 and is represented by a solid line in FIG. 10B. A similar outline of a crosscut 179' which occurs at face 90 is represented by dashed lines. Further, an outline of a crosscut 179" which occurs at face 124 is also represented by dashed lines. Note that each outline of each crosscut, 179, 179' and 179" has line segments of sides 102, 104, 106 and 108.

Valve Design Considerations

The following set of parameter calculations is provided for design clarification for a twisted slit valve for luer fitting applications: (It should be noted that these parameters are only exemplary and may be varied for different valve designs within the scope of the instant invention.)

Figure 16:
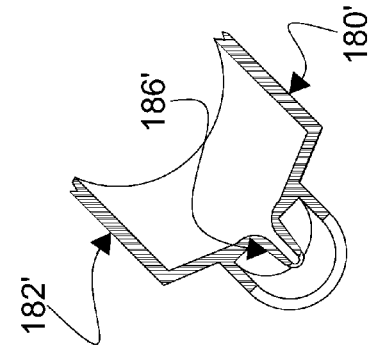
FIG. 16 is a cross section of a portion of a medical syringe with a shortened male fitting adapted for having a twisted slit valve device affixed thereto.
Figure 17:
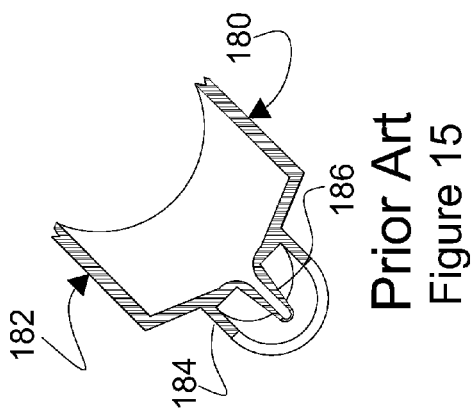
FIG. 17 is a cross section of the syringe seen in FIG. 16 with a twisted slit valve device affixed thereto and an associated female luer fitting section disposed for valve insertion.
Figure 18:
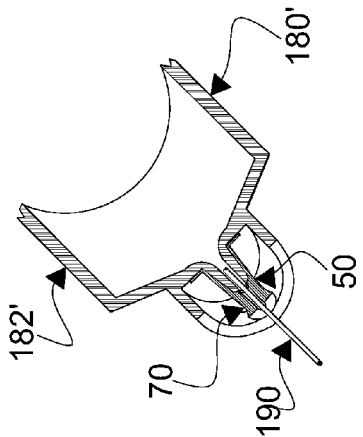
FIG. 18 is a cross section of parts seen in FIG. 17 with the female luer fitting disposed about the twisted male luer fitting device.

First, the following assumptions may be made:
Pitch or taper (α) of female luer fitting (such as fitting 170): α=3°
Diameter (δ) of luer fitting for opening smallest portion of valve 70: δ=0.152 inches
Desired diameter (χ) of through hole 177 (approx. a size 16 needle): χ=0.040 inches
Slit length (φ) based upon size of hole 177: φ=0.063 inches Valve Construct Ion Parameters Based upon the design considerations listed supra, the following valve parameters may be calculated:
For a cross section at face 90 (see FIGS. 4A and 5A)
Distance from face 90: 0.000 inches
Circular cross section diameter: δ=0.152 inches
Cross section circumference:(Sum of segments 102, 104, 106 & 108). γ=0.479 inches
Relative angle of rotation: 0°
Wall thickness (δ−χ): 0.056 inches
Radius of curvature of segments 102 and 106: 0.076 inches
Maximum cross section length (δ+φ): 0.175 inches
Cross section width: 0.112 inches
For a cross section at plane 178 (see FIG. 10A)
Distance from face 90: 0.050 inches
Circular cross section diameter (δ'): δ'=0.158 inches
Cross section circumference (Sum of segments 102, 104, 106 & 108): γ=0.495 inches
Relative angle of rotation: 45°
Wall thickness (δ'−χ): 0.058 inches
Radius of curvature of segments 102 and 106: 0.079 inches
Maximum cross section length (δ'+φ): 0.180 inches
Cross section width: 0.117 inches
For a cross section at internal face 124 (see FIGS. 4A and 5A)
Distance from face 90: 0.100 inches
Circular cross section diameter (δ"): δ"=0.163 inches
Cross section circumference:(Sum of segments 102, 104, 106 & 108). γ=0.512 inches
Relative angle of rotation: 90°
Wall thickness (δ"−χ): 0.061 inches
Radius of curvature of segments 102 and 106: 0.081 inches
Maximum cross section length (δ"+φ): 0.186 inches
Cross section width: 0.122 inches Note linear dimensional relationships among the calculated parameters Additional operational aspects of a twisted slit valve are shown in FIGS. 16-20. For reference, in FIG. 15, a section 180 of a PRIOR ART conventional syringe 182 is seen. Syringe 180 comprises a luer lock cylinder 184 and a conventional male luer fitting 186. A section 180' of similar syringe 182' made according to the instant invention is seen in FIG. 16. Syringe 182' comprises male luer fitting 186' for valve 50, as disclosed supra. Male luer fitting 186' is fitted with a device 50 in FIG. 17. Further, a conventional female luer fitting 170 is seen in alignment for device 50 insertion. In FIG. 18, device 50 (and male luer fitting 186' are displaced into female luer fitting 170, opening valve 70.

Figure 19:
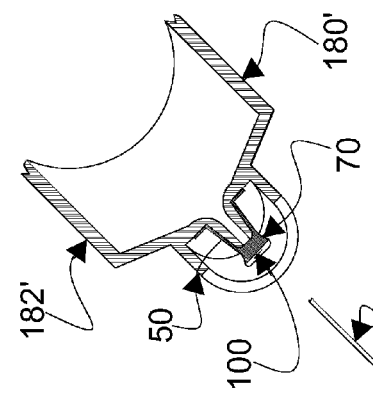
FIG. 19 is a cross section of a twisted slit valve device affixed thereto as seen in FIG. 17 with a hollow cannula disposed in line with the slit of the valve.
Figure 20:
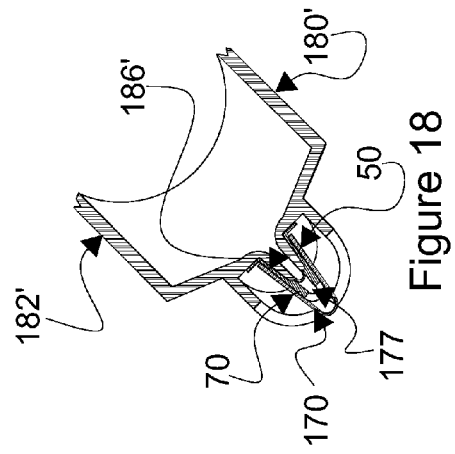
FIG. 20 is a cross section of parts seen in FIG. 17 with the female luer fitting disposed about the twisted male luer fitting device and the cannula displaced through an orifice made by slit displacement within the twisted slit valve.

In FIG. 19, a blunt cannula 190 is seen disposed in alignment with slot 100 (see FIG. 10 for a magnified view of slit 100) of valve 70 affixed to syringe 182'. Note in FIG. 20, blunt cannula 190 can pierce slit 100 to provide an open fluid path without compressive distortion of valve 70.

Reference is now made to FIGS. 21 and 22 where a plurality of twisted slit valves provides both a male and a female luer valve for a needleless connector and a needleless connector adapter combination. In FIG. 21, two valved apparatuses are seen. The first apparatus being a syringe barrel 30 with a twisted slit valve device 50 affixed to a male luer fitting 40 to provide combination 80 (see FIG. 2). The second being a needleless connector 200, a section of which is seen to comprise a twisted slit valve 70 affixed to a displaceable needleless valve device 210. Note that, in the same manner valve 70 of device 50 is opened by insertion into a luer fitting, valve 70 of device 210 is opened by compressive insertion into female luer fitting 212 of needleless connector 200. Thus, inserting valve device 50 into a luer fitting, which commonly contains device 210, and displacing both valves 70 results in opening of both valves 70 and, thus, an open pathway 220. By providing force of a restoring memory due to displacement of valves 70 within the luer fitting, both valves are self-closing and returned to the closed state seen in FIG. 21 when valve device 50 is displaced from needleless connector device 200.

Incising a Slit

Reference is now made to FIG. 14 wherein a valve device 50 is seen disposed preparatory for slitting of valve 70. While slitting may be accomplished in various ways, a way, for example, is to use a slitting tool 250, also seen in FIG. 14. Slitting tool 250 comprises a slot 252 comprising a side circumference 254 which is sized and shaped to permit displacement of a twisted valve 70, which is untwisted, when displaced therein. Tool 250 also comprises a slitting or incising device 260 (e.g. a knife blade), having a cutting width of the length of slit 100.

Slitting is accomplished by displacing face 90 into slot 252 in direction of arrow 262 while rotating valve device 50 in a direction indicated by arrow 264 to force twisted valve 70 into a substantially untwisted state. In such a state, a planar slit 100 (not seen in FIG. 14) is incised by knife 260. Once slit 100 incision is complete, displacing valve 70 from slot 252 permits memory associated with valve 70 to twist once more to its original formed or molded state, closing slit 100.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A male adapter valve connector device for tapered fittings which is self-closed when not being compressively distorted and which is selectively opened for fluid passage when compressively, radially distorted along a predetermined length thereof, said valve device comprising:
   a body comprising material having memory for retaining an original form in which it was made, said material further comprising characteristics of being incompressible, unreactive to contacting fluids, and flexible;
   said body comprising a connecting end and an oppositely disposed valve, said valve comprising a twisted portion;
   said twisted portion comprising a twisted slit therethrough, said slit being medially disposed within said twisted portion and within an outer surface comprising a cross-section of predetermined circumference to thereby be closed to fluid flow when not distorted;
   said cross-section being asymmetric having an elongated length dimension in line with said slit and a width dimension orthogonally disposed relative to said slit;
   said valve being closed when in a rest or undeformed state and opened, in one mode, by compressively distorting said twisted portion to adjust said length and width dimensions to the same measure and thereby effect said slit to an open state along the length of said twisted portion due to cross-sectional deformation.

2. A valve device according to claim 1 wherein said body portion comprising the valve has sufficient twist to maintain closure of said slit against a predetermined pressure applied through the connecting end.

3. A valving combination according to claim 2 comprising said valve device and a hollow cylindrical tube having an end orifice sized to receive said valve and a cross-sectional circumference which is tapered to deform said elongated length dimension when said valve is disposed thereat to part the slit and thereby open the valve.

4. A valving combination according to claim 3 wherein said circumference of said outer surface of said valve and said cross-sectional circumference of said tube correspond to provide a common mating interface.

5. A valving combination according to claim 4 wherein said hollow tube is a female luer fitting.

6. A valving combination according to claim 5 wherein said circumference of said outer surface of said valve comprises dimensions of a male luer fitting when compressively deformed within said female luer fitting.

7. A valving combination according to claim 2 further comprising a blunt cannula and wherein said body is disposed to receive said blunt cannula displaced through said slit to thereby open said valve in a second mode.

8. A valve according to claim 1 wherein said material is butyl rubber.

9. A valve according to claim 1 wherein said slit is planar in form.

* * * * *